United States Patent
Ohhigashi et al.

(10) Patent No.: US 11,724,975 B2
(45) Date of Patent: Aug. 15, 2023

(54) AZEOTROPE OR AZEOTROPIC COMPOSITION CONTAINING PENTAFLUOROPROPANE AND WATER, AND METHOD FOR PRODUCING PENTAFLUOROPROPANE

(71) Applicant: DAIKIN INDUSTRIES, LTD., Osaka (JP)

(72) Inventors: Yuuko Ohhigashi, Osaka (JP); Tatsuya Takakuwa, Osaka (JP); Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 17/677,355

(22) Filed: Feb. 22, 2022

(65) Prior Publication Data

US 2022/0177395 A1   Jun. 9, 2022

Related U.S. Application Data

(62) Division of application No. 16/622,372, filed as application No. PCT/JP2018/022977 on Jun. 15, 2018, now Pat. No. 11,286,222.

(30) Foreign Application Priority Data

Jun. 16, 2017   (JP) ................. 2017-118588

(51) Int. Cl.
   *C07C 17/383*   (2006.01)
   *C07C 17/08*   (2006.01)
   (Continued)

(52) U.S. Cl.
   CPC ............ *C07C 17/383* (2013.01); *C07C 19/08* (2013.01); *C09K 5/04* (2013.01)

(58) Field of Classification Search
   CPC ......... C07C 17/383; C07C 19/08; C09K 5/04; C09K 3/00
   See application file for complete search history.

(56) References Cited

U.S. PATENT DOCUMENTS 8,741,828 B2 *   6/2014   Hulse ................... C07C 17/383
                                                              510/408
8,853,473 B2 *  10/2014   Takahashi ............... C07C 21/18
                                                              570/178
(Continued)

FOREIGN PATENT DOCUMENTS

EP   2 326 613   3/2010
JP   2011-83726   4/2011

OTHER PUBLICATIONS

International Search Report dated Aug. 28, 2018 in International (PCT) Application No. PCT/JP2018/022977.
(Continued)

*Primary Examiner* — Joseph D Anthony
(74) *Attorney, Agent, or Firm* — Wenderoth, Lind & Ponack, L.L.P.

(57) ABSTRACT

An object of the present invention is to provide a method that can efficiently remove water contained in pentafluoropropane. Provided as a solution is a method comprising distilling a composition comprising pentafluoropropane and water to thereby extract pentafluoropropane with a water content higher than that of the composition as a first stream, and pentafluoropropane with a water content lower than that of the composition as a second stream.

1 Claim, 1 Drawing Sheet

(51) Int. Cl.
*C09K 5/04* (2006.01)
*C07C 19/08* (2006.01)

(56) References Cited

U.S. PATENT DOCUMENTS

| | | | | |
|---|---|---|---|---|
| RE46,928 E | * | 7/2018 | Hulse | C07C 17/389 |
| 2011/0027524 A1 | | 2/2011 | Bowland et al. | |
| 2011/0101264 A1 | * | 5/2011 | Knapp | C07C 17/386 |
| | | | | 252/67 |
| 2011/0160500 A1 | * | 6/2011 | Takahashi | C07C 21/18 |
| | | | | 570/175 |
| 2011/0201851 A1 | * | 8/2011 | Nose | C07C 17/383 |
| | | | | 570/154 |
| 2011/0275724 A1 | * | 11/2011 | Hulse | C07C 17/389 |
| | | | | 514/772 |
| 2012/0215039 A1 | * | 8/2012 | Hulse | C07C 21/04 |
| | | | | 570/160 |
| 2013/0065044 A1 | * | 3/2013 | Bowman | B32B 5/18 |
| | | | | 428/318.8 |
| 2014/0305161 A1 | * | 10/2014 | Kawaguchi | C07C 17/383 |
| | | | | 62/617 |
| 2014/0367606 A1 | * | 12/2014 | Takahashi | C07C 17/383 |
| | | | | 252/67 |
| 2015/0239808 A1 | * | 8/2015 | Sedat | C07C 17/25 |
| | | | | 570/155 |
| 2019/0127303 A1 | * | 5/2019 | Ondrus | B01D 3/14 |

OTHER PUBLICATIONS

Extended European Search Report dated Feb. 11, 2021 in corresponding European Patent Application No. 18817508.7.

* cited by examiner

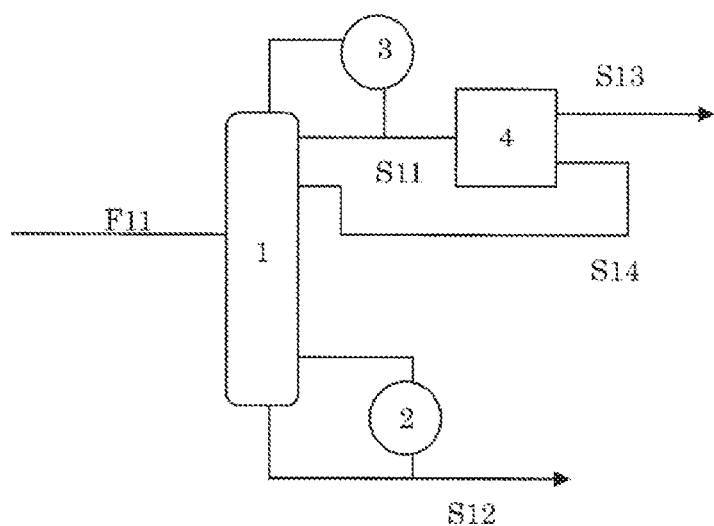

AZEOTROPE OR AZEOTROPIC COMPOSITION CONTAINING PENTAFLUOROPROPANE AND WATER, AND METHOD FOR PRODUCING PENTAFLUOROPROPANE

TECHNICAL FIELD

The present invention relates to an azeotropic or azeotrope-like composition comprising pentafluoropropane and water, and a method for producing pentafluoropropane with a reduced water content using the characteristic of the composition.

BACKGROUND ART

Alternative refrigerants, such as 1,1,1,2,2-pentafluoroethane (HFC-125) and difluoromethane (HFC-32), have been widely used as important substances that replace CFC, HCFC, etc., which destroy the ozone layer. However, these are potent global-warming substances, and there is a concern that the diffusion of these substances may affect global warming. As a measure against that, these substances are collected after use; however, not all of them can be collected, and diffusion by leakage etc. cannot be ignored. Alternatives by $CO_2$ and hydrocarbon substances have also been examined; however, $CO_2$ refrigerants have low efficiency, and large devices are required. Thus, there are many problems in comprehensive greenhouse gas emission reduction, including energy consumption. Moreover, hydrocarbon substances have safety problems due to their high flammability.

Pentafluoropropanes typified by 1,1,1,2,2-pentafluoropropane (HFC-245cb), 1,1,1,2,3-pentafluoropropane (HFC-245eb), and 1,1,1,3,3-pentafluoropropane (HFC-245fa) are expected as refrigerants that can solve the above problems. In addition, their applications as environmentally preferable cleaning agents, foaming agents, propellants, heat transfer media, fire extinguishers, etc., are also expected. Furthermore, the use of some of these pentafluoropropanes as intermediates for producing 2,3,3,3-tetrafluoropropene (HFO-1234yf, $CF_3CF=CH_2$) and 1,3,3,3-tetrafluoropropene (HFO-1234ze, $CF_3CH=CHF$), which are HFCs of olefins with a low warming coefficient, has attracted attention.

Pentafluoropropanes can be obtained by fluorinating corresponding chloride raw materials, such as 1,1,1,2,3-pentachloropropane (HCC-240db), 1,1,1,3,3-pentachloropropane (HCC-240fa), and 1,1,2,3-tetrachloropropene (HCO-1230xa), with HF by a vapor-phase or liquid-phase process in 1 to 3 steps. In these methods, HCl is produced as a by-product, and it is difficult to convert 100% of chloride (raw material) and HF. Accordingly, it is necessary to recycle them in the reaction process. When the reaction to remove HF from pentafluoropropane is performed, it is necessary to remove the produced HF, which inhibits new HF elimination reaction. Applicable methods are water washing, distillation, etc. The simplest method of removing HF from a mixed gas of pentafluoropropane and HF is a method of absorbing HF with water. However, in this method, the treated pentafluoropropane is inevitably contaminated with vapor mist, and water in an amount corresponding to the vapor pressure.

In addition, pentafluoropropane is often contaminated with water derived from various sources, such as water contained in the raw materials, water generated from the catalyst, and water remaining in the facility.

Water contained in pentafluoropropane affects the stability of pentafluoropropane, the corrosiveness of the apparatus, the ability as a refrigerant, etc., and is thus one of the important factors for quality control. The method of removing water is particularly an important technique.

Conventionally, a method using an adsorbent, such as a molecular sieve, is common. For example, PTL 1 described below discloses zeolite that can be applied to the drying of HFC-245fa. However, in this method, it is generally necessary to treat gas with a relatively low water concentration at high speed, which requires the use of a large dehydration column. In addition, it is necessary to regularly reproduce and exchange the adsorbent. There is also a problem in that a large amount of industrial waste is generated when the adsorbent is exchanged.

CITATION LIST

Patent Literature

PTL 1: JP2011-83726A

SUMMARY OF INVENTION

Technical Problem

The present invention was made in consideration of the current situation of the above prior art. A main object of the present invention is to provide a method that can efficiently remove water contained in pentafluoropropane.

Solution to Problem

The present inventors conducted extensive research to achieve the above object. As a result, the present inventors found a conventionally unknown phenomenon in which pentafluoropropane and water formed a minimum azeotropic composition (which is called a heterophase azeotropic composition when two liquid phases are formed). Then, the present inventors found that water contained in pentafluoropropane can be efficiently removed by using this characteristic. Thus, the present invention has been completed.

That is, the present invention provides the following azeotropic or azeotrope-like composition, and the following pentafluoropropane from which water is removed.

Item 1.

An azeotropic or azeotrope-like composition comprising 1,1,1,2,2-pentafluoropropane (HFC-245cb) and water.

Item 2.

An azeotropic or azeotrope-like composition comprising 1,1,1,2,3-pentafluoropropane (HFC-245eb) and water.

Item 3.

The azeotropic or azeotrope-like composition according to Item 1, wherein HFC-245cb and water are contained in an amount of 90 to 100 mass relative to the entire composition.

Item. 4

The azeotropic or azeotrope-like composition according to Item 1, wherein HFC-245eb and water are contained in an amount of 90 to 100 mass % relative to the entire composition.

Item. 5

A method for producing a composition comprising pentafluoropropane with a water content lower than that of a starting composition comprising pentafluoropropane and water, the method comprising:

(1) distilling the starting composition to thereby extract a pentafluoropropane-containing composition with a water content higher than that of the starting composition as a first stream, and a pentafluoropropane-containing composition with a water content lower than that of the starting composition as a second stream.

Item. 6

The method according to Item 5, wherein the distillation is performed within a pressure range of atmospheric pressure to 2 MPa.

Item 7.

The production method according to Item 5 or 6, further comprising:

(2) cooling the composition of the first stream obtained in step (1) to induce liquid-liquid separation to form a phase A containing a larger amount of water and a phase B containing a larger amount of pentafluoropropane.

Item 8.

The method according to Item 7, further comprising: (3) subjecting the phase B separated in step (2) to step (1) as a composition comprising pentafluoropropane and water.

Item 9.

The method according to any one of Items 5 to 8, wherein the pentafluoropropane is at least one pentafluoropropane selected from the group consisting of HFC-245cb, HFC-245eb, and 1,1,1,3,3-pentafluoropropane (HFC-245fa).

Advantageous Effects of Invention

According to the method of the present invention, water can be efficiently removed from water-containing pentafluoropropane obtained by various synthesis methods, by performing distillation operation using the azeotropic phenomenon of pentafluoropropane and water, and further inducing liquid-liquid separation, if necessary.

BRIEF DESCRIPTION OF DRAWING

FIG. 1 is a flow diagram showing the outline of operation in Examples 1 and 2.

The azeotropic or azeotrope-like composition of the present invention, and the method for producing pentafluoropropane from which water is removed are described in detail below.

In the present specification, the term "azeotropic composition" refers to a composition in which vapor balanced with a mixed liquid has the same formulation as that of the mixed liquid. Specifically, this term refers to a composition in which, when the liquid phase is a homogeneous phase, there is no pressure difference between the boiling point curve and the dew point curve (based on the pressure of the boiling point curve). In a heterophase azeotropic composition in which two liquid phases are formed, the two-liquid phase region shows a predetermined vapor phase formulation; thus, the condensed liquid is considered to be an azeotropic composition. The term "azeotropic composition" in the present specification also includes a heterophase azeotropic composition.

In the present specification, the term "azeotrope-like composition" refers to a composition in which vapor balanced with a mixed liquid has a similar formulation to that of the mixed liquid.

In the present specification, the terms "concentrate" and "remove" are used in opposing concepts. That is, when a component in a mixture is concentrated, components other than this component are supposed to be removed.

1. Azeotropic or Azeotrope-Like Composition

The azeotropic or azeotrope-like composition of the present invention comprises at least HFC-245cb or HFC-245eb, and water. The azeotropic or azeotrope-like composition of the present invention may consist of HFC-245cb or HFC-245eb, and water; or may further contain other additional compounds, in addition to HFC-245cb or HFC-245eb, and water.

The study of the present inventors found a phenomenon in which when a mixture of HFC-245cb or HFC-245eb, and water was distilled, water was concentrated toward the top of the distillation column, and when a fixed water concentration was reached, the concentration did not increase any more.

When the liquid phase is a homogeneous phase, the azeotrope-like composition of the present invention is preferably a composition in which the pressure difference between the boiling point curve and the dew point curve is within 5% (based on the pressure of the boiling point curve).

The additional compounds are not limited, and examples include saturated or unsaturated halogenated hydrocarbons. The saturated or unsaturated halogenated hydrocarbons are preferably fluoridated hydrocarbon and chlorinated hydrocarbon, and more preferably $C_{1-3}$ fluoridated hydrocarbon and chlorinated hydrocarbon.

Specific examples of the additional compounds include the following compound group. The azeotropic or azeotrope-like composition of the present invention may contain these compounds singly or in combination of two or more (when HFC-245cb or HFC-245eb is not an essential component, these are contained as additional compounds in the azeotropic or azeotrope-like composition of the present invention).

$CF_3CF=CH_2$ (2,3,3,3-tetrafluoropropene, HFO-1234yf)
$CF_3CH=CHF$ (1,3,3,3-tetrafluoropropene, HFO-1234ze)
$CF_3CHFCH_3$ (1,1,1,2,3-tetrafluoropropane, HFC-254eb)
$CF_3CH=CH_2$ (3,3,3-trifluoropropene, HFO-1243zf)
$CF_3CHFCH_2F$ (1,2,3,3,3-pentafluoropropane, HFC-245eb)
$CF_3CH_2CHF_2$ (1,1,1,3,3-pentafluoropropane, HFC-245fa)
$CF_3CF_2CH_3$ (1,1,1,2,2-pentafluoropropane, HFC-245cb)
$CF_3CHFCHF_2$ (1,1,1,2,3,3-hexafluoropropane, HCFC-236ea)
$CF_3CH_2CF_3$ (1,1,1,3,3,3-hexafluoropropane, HFC-236fa)
$CF_3CF=CHF$ (1,2,3,3,3-pentafluoropropene, HFO-1225ye)
$CF_3CCH$ (3,3,3-trifluoropropyne)
$CHF_3$ (fluoromethane, HFC-23)
$CH_2F_2$ (difluoromethane, HFC-32)
$CF_3CHF_2$ (1,1,1,2,2-pentafluoroethane, HFC-125)
$CF_3CH_2F$ (1,1,1,2-tetrafluoroethane, HFC-134a)
$CF_3CF=CF_2$ (hexafluoropropene, FC-1216)
$CHCl_3$ (trichloromethane)

For example, the azeotropic or azeotrope-like composition of the present invention is obtained by removing HF by water washing from a product of reaction to obtain HFO-1234yf by HF elimination reaction of HFC-245cb or HFC-245eb, followed by distillation. In this example, HFO-1234ze contained in the azeotropic or azeotrope-like composition can serve as an additional compound.

The total content ratio of the additional compounds relative to the entire composition is preferably 10 mass % or less, more preferably 5 mass % or less, and even more preferably 1 mass % or less. The additional compounds are generally contained in a total amount of 0.1 mass % or more, preferably 0.01 mass % or more, and more preferably 0.001 mass % or more.

In a preferable embodiment, the azeotropic or azeotrope-like composition of the present invention consists of a two-component azeotropic or azeotrope-like composition consisting of HFC-245cb and water, and other additional compounds. In this embodiment, the total content ratio of the additional compounds relative to the entire composition is preferably 5 mass % or less, more preferably 1 mass % or less, and even more preferably 0.5 mass % or less. Because the total content ratio of the additional compounds is controlled within the above range, the azeotropic or azeotrope-like composition of the present invention exhibits, as a whole, characteristics as an azeotropic or azeotrope-like composition.

In the azeotropic composition, the azeotropic formulation shows a fixed value depending on temperature and pressure. When temperature and pressure change, the azeotropic formulation may also change. For example, in a composition consisting of HFC-245cb and water, a formulation consisting of 99.12 mass % of HFC-245cb and 0.88 mass % of water is an azeotropic formulation at a pressure of 0.57 MPa and a temperature of 32° C. Further, in a composition consisting of HFC-245eb and water, a formulation consisting of 75.5 mass % of HFC-245eb and 24.5 mass % of water is an azeotropic formulation at a pressure of 0.129 MPa and a temperature of 25° C.

Moreover, formulations similar to the above formulations can be handled in the substantially same manner as azeotropic compositions (that is, compositions having such formulations are azeotrope-like compositions).

The two-component azeotropic or azeotrope-like composition consisting of HFC-245cb and water more preferably contains 2 to 99.995 mass % or 96 to 99.995 mass % of HFC-245cb relative to the entire two-component composition. In this range, when the composition is azeotropic (including heterophase azeotropic), or when the liquid phase is a homogeneous phase, within a pressure range of atmospheric pressure (0.1013 MPa) to 2 MPa, the pressure difference between the boiling point curve and the dew point curve is within 5%; that is, the composition becomes azeotrope-like (based on the pressure of the boiling point curve). Moreover, the two-component azeotropic or azeotrope-like composition more preferably further contains 95 to 100 mass % or 99 to 100 mass % of HFC-245cb relative to the entire two-component composition. In this range, when the composition is azeotropic (including heterophase azeotropic), or when the liquid phase is a homogeneous phase, within a pressure range of atmospheric pressure (0.1013 MPa) to 2 MPa, the pressure difference between the boiling point curve and the dew point curve is within 5%; that is, the composition becomes more azeotrope-like (based on the pressure of the boiling point curve).

The two-component azeotropic or azeotrope-like composition consisting of HFC-245eb and water more preferably contains 10 to 99.995 mass % or 98 to 99.995 mass % of HFC-245eb relative to the entire two-component composition. In this range, when the composition is azeotropic (including heterophase azeotropic), or when the liquid phase is a homogeneous phase, within a pressure range of atmospheric pressure (0.1013 MPa) to 2 MPa, the pressure difference between the boiling point curve and the dew point curve is within 5%; that is, the composition becomes azeotrope-like (based on the pressure of the boiling point curve). Further, the two-component azeotropic or azeotrope-like composition more preferably contains 95 to 100 mass % or 99 to 100 mass % of HFC-245eb relative to the entire two-component composition. In this range, when the composition is azeotropic (including heterophase azeotropic), or when the liquid phase is a homogeneous phase, within a pressure range of atmospheric pressure (0.1013 MPa) to 2 MPa, the pressure difference between the boiling point curve and the dew point curve is within 5%; that is, the composition becomes more azeotrope-like (based on the pressure of the boiling point curve).

The distillation is preferably performed within a pressure range of atmospheric pressure (0.1013 MPa) to 2 MPa. A pressure equal to or higher than atmospheric pressure is preferable, because the reflux temperature decreases, thereby reducing the possibility of liquid separation in the column. Further, a pressure of 2 MPa or less is preferable, because the operating temperature increases, and the heating amount increases, thereby reducing the possibility of inefficiency.

2. Method for Producing Pentafluoropropane with Reduced Water Content

The method for producing pentafluoropropane with a reduced water content of the present invention comprises:

(1) distilling a composition comprising pentafluoropropane and water to thereby extract a pentafluoropropane-containing composition with a water content higher than that of the composition as a first stream, and a pentafluoropropane-containing composition with a water content lower than that of the composition as a second stream.

The pentafluoropropane is preferably at least one pentafluoropropane selected from the group consisting of HFC-245cb, HFC-245eb, and HFC-245fa. The composition comprising pentafluoropropane and water may contain one or more of these pentafluoropropanes.

The composition comprising pentafluoropropane and water preferably contains at least one pentafluoropropane at a content ratio higher than other pentafluoropropanes. In this case, in the composition comprising pentafluoropropane and water, the total content ratio of the other pentafluoropropanes relative to the entire composition is preferably 20 mass % or less, more preferably 10 mass % or less, and even more preferably 2 mass % or less. The at least one pentafluoropropane, which is contained at a content ratio higher than other pentafluoropropanes, is preferably HFC-245cb.

The composition comprising pentafluoropropane and water may further contain the additional compounds described in section 1 above. In this case, when the composition comprising pentafluoropropane and water contains at least one pentafluoropropane at a content ratio higher than other pentafluoropropanes, the total content ratio of the additional compounds and the other pentafluoropropanes is preferably 10 mass % or less, more preferably 5 mass % or less, and even more preferably 1 masse or less.

The distillation pressure is not limited, and can be set in a wide range. For example, the pressure can be set from about atmospheric pressure (0.1013 MPa) to 2 MPa. The distillation pressure is preferably set in a range of 0.4 MPa to 2 MPa, because an overly low pressure lowers the reflux temperature, thereby reducing the possibility of liquid separation in the column.

When the composition comprising pentafluoropropane and water, in which the water content is less than the above azeotropic formulation, is distilled by this distillation operation, a pentafluoropropane-containing composition with a concentrated water content, i.e., a pentafluoropropane-containing composition with a water content higher than that of the composition supplied to the distillation column, is obtained from the column top of the distillation column (first stream).

When the pentafluoropropane-containing composition with a concentrated water content (first stream) obtained from the column top in step (1) is dried using an adsorbent, such as a molecular sieve, the size of the drying column necessary for drying can be reduced, compared with conventional drying methods.

The pentafluoropropane-containing composition with a reduced water content (second stream) obtained from the column bottom in step (1) can also be dried using an adsorbent, such as a molecular sieve.

When the composition comprising pentafluoropropane and water is distilled, the additional compounds can be extracted together with pentafluoropropane, and separated in another distillation column.

The production method of the present invention may further comprise the following step (2), if necessary:

(2) cooling the composition of the first stream obtained in step (1) to induce liquid-liquid separation to form a phase A containing a larger amount of water and a phase B containing a larger amount of pentafluoropropane.

Thus, the pentafluoropropane-containing composition (first stream) obtained from the column top is cooled using a decanter or the like to induce liquid-liquid separation to form a phase A containing a larger amount of water and a phase B containing a larger amount of pentafluoropropane, whereby water can be efficiently separated.

In the decanter, liquid-liquid separation may occur by cooling to a temperature lower than the pentafluoropropane-containing composition extracted from the distillation column. The temperature can be widely selected within a range in which the separated water does not freeze. For example, the temperature can be set to 5 to 50° C.

Water can be efficiently separated by performing the above distillation operation and liquid-liquid separation as a continuous operation.

The phase A containing a large amount of water separated in the above manner may be discarded. Further, the phase B containing a larger amount of pentafluoropropane can be returned to the rectification column and rectified again. When only the phase B is dried by a molecular sieve, the size of the drying column necessary for drying can be significantly reduced.

BEST MODE FOR CARRYING OUT THE INVENTION

The present invention is described in more detail below with reference to Examples.

Example 1

Table 1 shows the data of the phase equilibrium between HFC-245cb and water at 0.57 MPa.

TABLE 1

| x(245cb) | y(245cb) | T(° C.) |
|---|---|---|
| 0.0 | 0 | 157.0 |
| 5.0 | 99.12 | 32.0 |
| 10.0 | 99.12 | 32.0 |
| 20.0 | 99.12 | 32.0 |
| 30.0 | 99.12 | 32.0 |
| 40.0 | 99.12 | 32.0 |
| 50.0 | 99.12 | 32.0 |
| 60.0 | 99.12 | 32.0 |
| 70.0 | 99.12 | 32.0 |
| 80.0 | 99.12 | 32.0 |
| 90.0 | 99.12 | 32.0 |
| 99.0 | 99.12 | 32.0 |
| 99.75 | 99.17 | 32.0 |
| 99.84 | 99.48 | 32.1 |

TABLE 1-continued

| x(245cb) | y(245cb) | T(° C.) |
|---|---|---|
| 99.90 | 99.67 | 32.2 |
| 99.96 | 99.87 | 32.2 |
| 100.0 | 100.0 | 32.3 |

As shown in Table 1, it is found that there are two phases in the formations in which the 245cb ratio is between 5% and 99%.

Table 2 shows the results of distilling HFC-245cb containing water with an inlet water concentration of 200 ppm using a distillation column having a theoretical plate number of 20. FIG. 1 shows a schematic diagram of the distillation column. The pressure was 0.57 MPa, the column top temperature was 32° C., and the column bottom temperature was 35° C. In FIG. 1, F11 represents the supplied gas, and S11 to S14 represent streams.

TABLE 2

| Water concentration (unit: mass) | | | | |
|---|---|---|---|---|
| F11 | S11 | S12 | S13 | S14 |
| 200 ppm | 3500 ppm | <1 ppm | >99% | 2600 ppm |

Operating pressure: 0.47 MPaG
Top temperature: 32° C.
Bottom temperature: 35° C.

Example 2

Table 3 shows the data of the phase equilibrium between HFC-245eb and water at 25° C.

TABLE 3

| x(245eb) | y(245eb) | P(MPa) |
|---|---|---|
| 0.0 | 0 | −0.098 |
| 1.0 | 75.5 | −0.069 |
| 2.0 | 75.5 | −0.050 |
| 5.0 | 75.5 | −0.02 |
| 10.0 | 75.5 | 0.129 |
| 20.0 | 75.5 | 0.129 |
| 30.0 | 75.5 | 0.129 |
| 40.0 | 75.5 | 0.129 |
| 50.0 | 75.5 | 0.129 |
| 60.0 | 75.5 | 0.129 |
| 70.0 | 75.5 | 0.129 |
| 80.0 | 75.5 | 0.129 |
| 90.0 | 75.5 | 0.129 |
| 98.0 | 75.5 | 0.12 |
| 99.9 | 99.5 | 0.115 |
| 100.0 | 100 | 0.113 |

Because the vapor pressure of the compositions of 245eb and water is higher than that of each pure substance, it is found that these compositions are azeotropic. At least the formulations in which the 245eb ratio is between 10% and 90% are considered to be heterophase azeotropic.

REFERENCE SIGNS LIST

1. Rectification column
2. Reboiler
3. Capacitor
4. Decanter

The invention claimed is:

1. An azeotropic or azeotrope-like composition comprising 1,1,1,2,3-pentafluoropropane (HFC-245eb) and water, wherein the HFC-245 eb and water are contained in an amount of 90 to 100 mass % relative to the entire composition.

* * * * *